United States Patent
Amako et al.

(10) Patent No.: US 8,836,946 B2
(45) Date of Patent: Sep. 16, 2014

(54) OPTICAL DEVICE AND DETECTION DEVICE

(75) Inventors: Jun Amako, Tsurugashima (JP); Kohei Yamada, Minowa (JP); Tatsunori Miyazawa, Chino (JP)

(73) Assignee: Seiko Epson Corporation (JP)

( * ) Notice: Subject to any disclaimer, the term of this patent is extended or adjusted under 35 U.S.C. 154(b) by 263 days.

(21) Appl. No.: 13/530,741

(22) Filed: Jun. 22, 2012

(65) Prior Publication Data

US 2012/0327417 A1 Dec. 27, 2012

(30) Foreign Application Priority Data

Jun. 23, 2011 (JP) ................. 2011-139526

(51) Int. Cl.
- *G01N 21/55* (2014.01)
- *G01N 21/47* (2006.01)
- *G01N 21/65* (2006.01)
- *B82Y 20/00* (2011.01)
- *G01J 3/44* (2006.01)
- *B82Y 15/00* (2011.01)

(52) U.S. Cl.
CPC ............... *G01N 21/658* (2013.01); *B82Y 15/00* (2013.01); *B82Y 20/00* (2013.01)
USPC ............................ 356/445; 356/446; 356/301

(58) Field of Classification Search
None
See application file for complete search history.

(56) References Cited

U.S. PATENT DOCUMENTS

| | | | |
|---|---|---|---|
| 7,079,250 B2 | 7/2006 | Mukai | |
| 7,399,445 B2 | 7/2008 | Kuroda et al. | |
| 7,483,130 B2 | 1/2009 | Baumberg et al. | |
| 7,733,491 B2 | 6/2010 | Kuroda et al. | |
| 7,864,313 B2 | 1/2011 | Baumberg et al. | |
| 8,085,405 B2 | 12/2011 | Ogawa | |
| 2010/0085566 A1 | 4/2010 | Cunningham | |
| 2011/0114859 A1 | 5/2011 | Amako et al. | |
| 2011/0116088 A1 | 5/2011 | Amako et al. | |

FOREIGN PATENT DOCUMENTS

| | | |
|---|---|---|
| JP | 2000-356587 | 12/2000 |
| JP | 2003-268592 | 9/2003 |
| JP | 2003-270132 | 9/2003 |
| JP | 2007-240361 | 9/2007 |
| JP | 2007-248284 | 9/2007 |
| JP | 2007-303973 | 11/2007 |

(Continued)

OTHER PUBLICATIONS

Chu, Yizhuo et al., "Experimental Study of the Interaction Between Localized and Propagating Surface Plasmons", School of Engineering and Applied Sciences, Harvard University, Optics Letters, vol. 34, No. 3, pp. 244-246, Aug. 18, 2008.

(Continued)

*Primary Examiner* — Michael A Lyons
*Assistant Examiner* — Amanda Merlino
(74) *Attorney, Agent, or Firm* — Harness, Dickey & Pierce, P.L.C.

(57) ABSTRACT

An optical device includes a group of projections projecting from a conductor surface of a substrate, and arranged along a first direction at a pitch Px, a dielectric layer covering the conductor surface and the group of projections, and a metal nanostructure having metal nanoparticles each having a size d of the order of nanometers arranged on the dielectric layer along the first direction, assuming that the wavelength of irradiation light is $\lambda$, $\lambda > Px > d$ is fulfilled, and assuming that a maximum value of an arrangement pitch between two of the metal nanoparticles adjacent to each other in the first direction is Qx, Px>Qx is fulfilled.

14 Claims, 11 Drawing Sheets

(56) References Cited

FOREIGN PATENT DOCUMENTS

| JP | 2010-025753 | 2/2010 |
|---|---|---|
| JP | 2011-128133 | 6/2011 |
| JP | 2011-128135 | 6/2011 |
| JP | 2011-141264 | 7/2011 |
| JP | 2011-141265 | 7/2011 |
| JP | 4801085 | 8/2011 |

OTHER PUBLICATIONS

Inoue, Masahiro et al., "Surface Enhanced Raman Scattering by Metal Spheres. I. Cluster Effect", Journal of the Physical Society of Japan, vol. 52, No. 11, pp. 3853-3864, Nov. 1983.

ously on the SiO$_2$ layer 50 at a pitch P=780 nm.

OPTICAL DEVICE AND DETECTION DEVICE

BACKGROUND

1. Technical Field

The present invention relates to an optical device, a detection device, and so on.

2. Related Art

In recent years, demand for sensors used, for example, for medical diagnostics or inspections of food and drink has increased, and further, development of a highly sensitive and small sized sensor has been demanded. In order to meet such a demand, a variety of types of sensors such as a sensor using an electrochemical process have been studied. Among these sensors, sensors using surface plasmon resonance (SPR) have been receiving increasing attention on the ground of possibility of integration, low cost, and applicability in all measurement environments.

For example, in JP-A-2000-356587 (Patent document 1), there is disclosed a method of using localized surface plasmon resonance (LSPR) to thereby improve sensor sensitivity.

In "Experimental study of the interaction between localized and propagating surface plasmons" (OPTICS LETTERS/Vol. 34, No. 3/Feb. 1, 2009; Non-patent document 1), there is disclosed a method of using both of propagating surface plasmon (PSP) and localized surface plasmon (LSP) to thereby improve the sensor sensitivity.

As shown in FIG. 1, in the patent document 1, fine metal particles 20 are fixed on a surface of a transparent substrate 10, and the transparent substrate 10 is irradiated with incident light to thereby measure the absorbance of the fine metal particles 20. As shown in FIG. 2, if a target object adheres the fine metal particles 20, a change from an absorbance spectrum indicated by A1 to an absorbance spectrum indicated by A2 occurs. According to the method of the patent document 1, a change in a medium in the vicinity of the fine metal particles is detected due to the change in the absorbance to thereby detect adsorption or deposition of the target object.

However, in this method, it is difficult to manufacture the fine metal particles so as to have uniform dimensions and shape, and to regularly arrange the fine metal particles. If the sizes and the arrangement of the fine metal particles fail to be controlled, variations are also caused in absorption and resonant wavelength generated by the plasmon resonance. Therefore, as shown in FIG. 2, the width of the absorbance spectrum becomes broader, and a peak intensity is lowered. Further, if the peak intensity is lowered, a signal variation for detecting the variation in the medium in the vicinity of the fine metal particles becomes smaller, and there arises a limitation in the improvement in the sensor sensitivity. Therefore, in such a usage of identifying a material based on the absorbance spectrum, it results that the sensor sensitivity is insufficient.

Moreover, since a surface enhanced Raman scattering (SERS) sensor in the related art only uses one of resonance peaks, it is required to fit the wavelength of the resonance peak to either one of an excitation wavelength and a Raman scattering wavelength. In this case, it results that only an electric field enhancement effect in either one of scattering processes is used, and therefore, a high electric field enhancement effect cannot be expected.

Meanwhile, in the Non-patent document 2, as shown in FIG. 3, there is disclosed a sensor provided with an Au film 40 having a thickness of 100 nm bonded to a glass substrate 30, an SiO$_2$ layer 50 having a thickness of 20 nm formed on the Au film 40, and a plurality of Au disks 60 each having diameter in a range of 100 through 170 nm arranged two-dimensionally on the SiO$_2$ layer 50 at a pitch P=780 nm.

In the sensor, there is excited the propagating surface plasmon PSP in an interface between the Au film 40 and the SiO$_2$ layer 50, and there is excited the localized surface plasmon LSP in the Au disks 60. Here, the propagating surface plasmon PSP is coupled to an evanescent field having a "wave number." The "wave number" is determined by the pitch P of the Au disks 60 to $2\pi/P$. Therefore, the pitch P of the Au disks 60 has a correlation with the excitation of the propagating surface plasmon PSP, and therefore, has a correlation with the resonance peak wavelength set in accordance with the Raman scattering wavelength of a sample, and cannot be changed freely.

On the other hand, the Au disks 60 each have a function as a hot site where a localized electrical field is enhanced, and in order for improving the sensitivity of the sensor, it is required for the hot sites to have a high density. However, the pitch P of the Au disks 60 determining the "wave number" of the propagating surface plasmon PSP is as relatively large as 780 nm, and the density of the hot sites becomes remarkably low. However, if an outer dimension of the Au disks 60 is increased while keeping the pitch P large, the resonant wavelength is shifted from the excitation wavelength on the longer wavelength side (the red side), and therefore, a strong localized electrical field cannot be expected.

SUMMARY

An advantage of some aspects of the invention is to provide an optical device determining a "wave number" of a propagating surface plasmon PSP independently of an arrangement pitch of metal nanoparticles while using both of propagating surface plasmon and localized surface plasmon to thereby make it possible to raise a density of the metal nanoparticles functioning as hot sites, and a detection device using the optical device.

(1) An aspect of the invention is directed to an optical device including a group of projections projecting from a conductor surface of a substrate, and arranged along a first direction at a pitch Px, a dielectric layer covering the conductor surface and the group of projections, and a metal nanostructure having metal nanoparticles each having a size d of the order of nanometers arranged on the dielectric layer along the first direction, wherein assuming that the wavelength of irradiation light is $\lambda$, $\lambda > Px > d$ is fulfilled, and assuming that a maximum value of an arrangement pitch between two of the metal nanoparticles adjacent to each other in the first direction is Qx, Px>Qx is fulfilled.

According to this aspect of the invention, the propagating surface plasmon PSP is excited on an interface between the conductor surface and the group of projections, and the dielectric layer, and a localized surface plasmon LSP is excited in the metal nanoparticles. Since the group of projections are arranged along the first direction at the pitch Px, the "wave number" of the propagating surface plasmon PSP is set based on the pitch Px of the group of projections, and does not depend on the arrangement pitch of the metal nanoparticles. The metal nanoparticles are not required to be arranged periodically.

Further, by fulfilling Px>d and Px>Qx, the density of the metal nanoparticles functioning as the hot sites can be raised. It should be noted that by irradiating the metal nanoparticles having a size d ($\lambda > d$) smaller than the wavelength $\lambda$ of incident light with the incident light, localized surface plasmon resonance (LSPR) can be used.

(2) In one aspect of the invention, the optical device may be configured such that Px/10>Qx is fulfilled, and ten or more of the metal nanoparticles are arranged within the pitch Px along the first direction. According to this configuration, the density of the metal nanoparticles functioning as the hot sites can further be raised.

(3) In one aspect of the invention, the optical device may be configured such that the group of projections are arranged along a second direction perpendicular to the first direction at a pitch Py, λ>Py>d is fulfilled, and assuming that a maximum value of an arrangement pitch between two of the metal nanoparticles adjacent to each other in the second direction is Qy, Py>Qy is fulfilled. According to this configuration, the density of the metal nanoparticles functioning as the hot sites in a two-dimensional plane can be raised.

(4) In one aspect of the invention, the optical device may be configured such that Py/10>Qy is fulfilled, and ten or more of the metal nanoparticles are arranged within the pitch Py along the second direction. According to this configuration, the density of the metal nanoparticles functioning as the hot sites in the two-dimensional plane can further be raised.

(5) In one aspect of the invention, the optical device may be configured such that the metal nanoparticles are arranged in the first direction at a constant pitch Qx. According to this configuration, it is possible to generate two resonance peaks.

(6) In one aspect of the invention, the optical device may be configured such that the metal nanoparticles are arranged in the second direction at a constant pitch py. According to this configuration, a dramatic electrical field enhancement effect can be obtained in the two-dimensional plane.

(7) In one aspect of the invention, the optical device may be configured such that the thickness of the dielectric film is equal to or smaller than 100 nm. Although a degree of enhancement of an electrical field significantly depends on the thickness of the dielectric layer, by setting the thickness of the dielectric layer to be equal to or smaller than 100 nm, the degree of enhancement of the electrical field can be kept to be higher than a certain level.

(8) Another aspect of the invention is directed to a detection device including the optical device described above, a light source, and a light detection section, a sample is introduced in the metal nanostructure of the optical device, the optical device emits light reflecting the sample in response to irradiation of light from the light source, and the light detection section detects the light reflecting the sample from the optical device. The detection device becomes capable of performing highly sensitive detection applying a surface enhanced Raman scattering.

BRIEF DESCRIPTION OF THE DRAWINGS

The invention will be described with reference to the accompanying drawings, wherein like numbers reference like elements.

DESCRIPTION OF AN EXEMPLARY EMBODIMENT

Hereinafter, a preferred embodiment of the invention will be described in detail. It should be noted that the present embodiment explained below does not unreasonably limit the content of the invention as set forth in the appended claims, and all of the constituents set forth in the present embodiment are not necessarily essential as means of the invention for solving the problems.

1. Detection Principle

Figure 1:
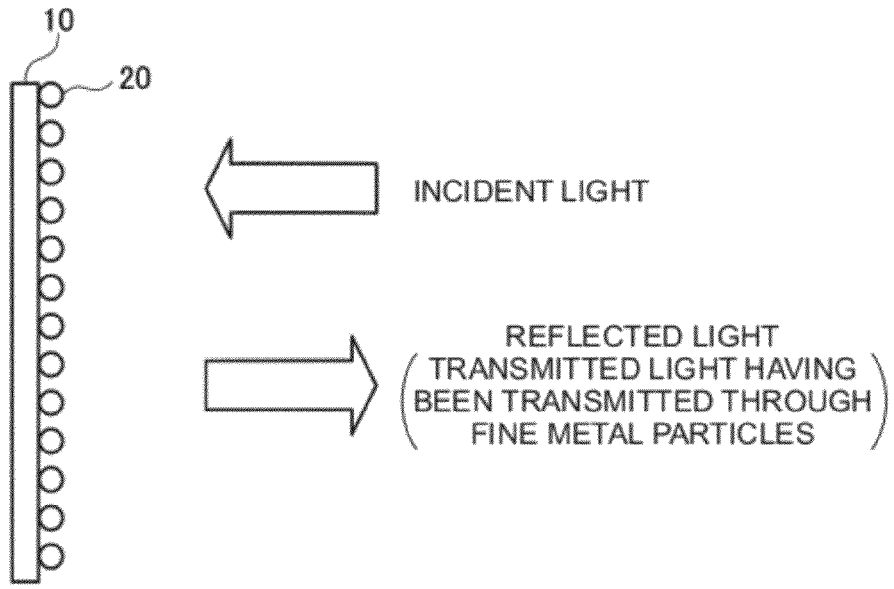
FIG. 1 is a diagram showing a sensor using localized surface plasmon according to the related art.
Figure 2:
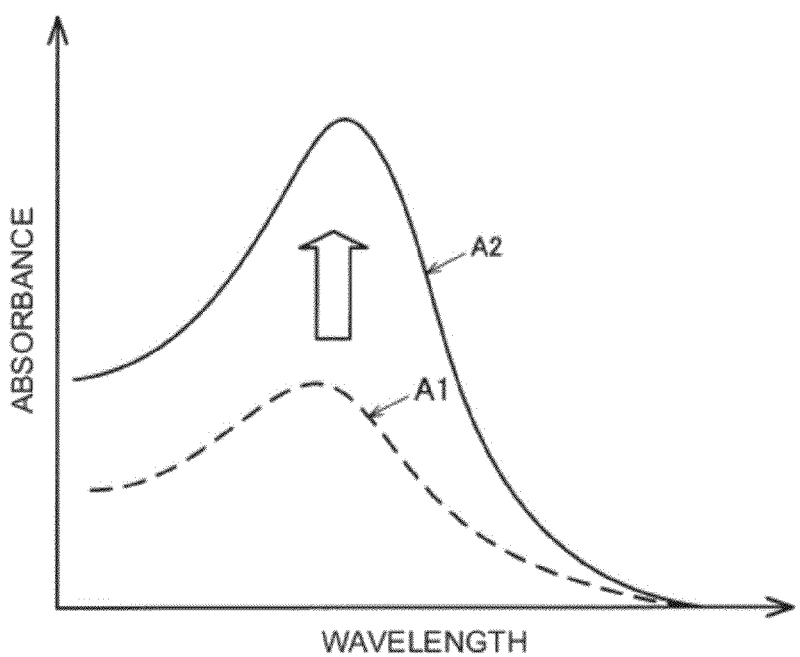
FIG. 2 is a characteristic diagram showing an absorbance spectrum of the sensor shown in FIG. 1.
Figure 3:
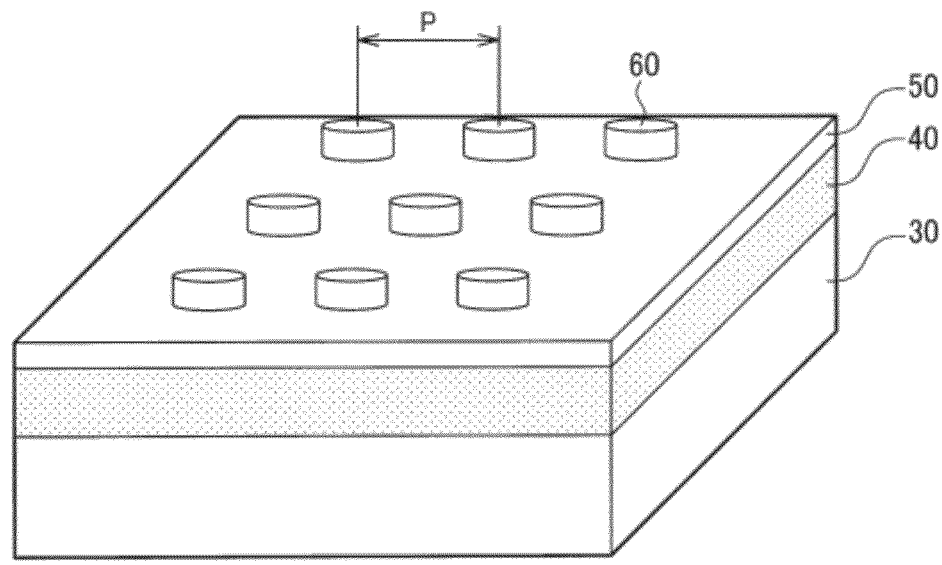
FIG. 3 is a diagram showing a sensor using both of propagating surface plasmon and the localized surface plasmon according to the related art.
Figure 4A:
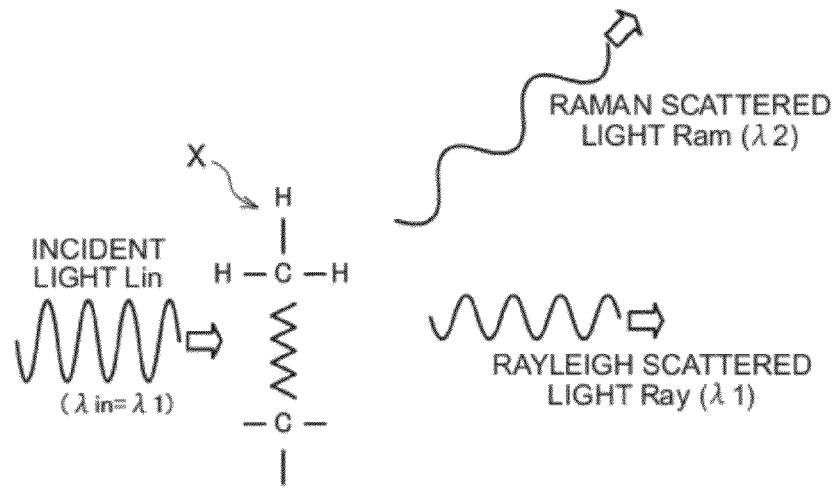
FIG. 4A is a fundamental explanatory diagram of Raman scattering spectroscopy.

FIG. 4A shows a fundamental explanatory diagram of Raman scattering spectroscopy. As shown in FIG. 4A, when irradiating a target molecule X (a target object) with a single-wavelength light Lin, a Raman scattered light Ram having a wavelength λ2 different from a wavelength λin of the incident light Lin is generated in a scattered light. A difference in energy between the Raman scattered light Ram and the incident light Lin corresponds to energy of a vibration level of the target molecule X, a rotation level, and an electron level thereof. Since the target molecule X has unique vibration energy corresponding to the structure thereof, by using the single-wavelength light Lin, the target molecule X can be identified.

For example, assuming that vibration energy of the incident light Lin is V1, the vibration energy of the target molecule X is V2, and vibration energy of the Raman scattered light Ram is V3, V3=V1−V2 is fulfilled. In other words, since the vibration energy V3 becomes vibration energy corresponding to the vibration energy V2, by measuring the wavelength λ2 of the Raman scattered light Ram, the target molecule X can be identified.

It should be noted that the most part of the incident light Lin has the same amount of energy after colliding with the target molecule X as that before the collision. This elastic scattered light is called a Rayleigh scattered light Ray. For example, assuming vibration energy of the Rayleigh scattered light Ray as V4, V4=V1 is fulfilled. Therefore, a wavelength λ1 of the Rayleigh scattered light Ray fulfills λ1=λin.

Figure 4B:
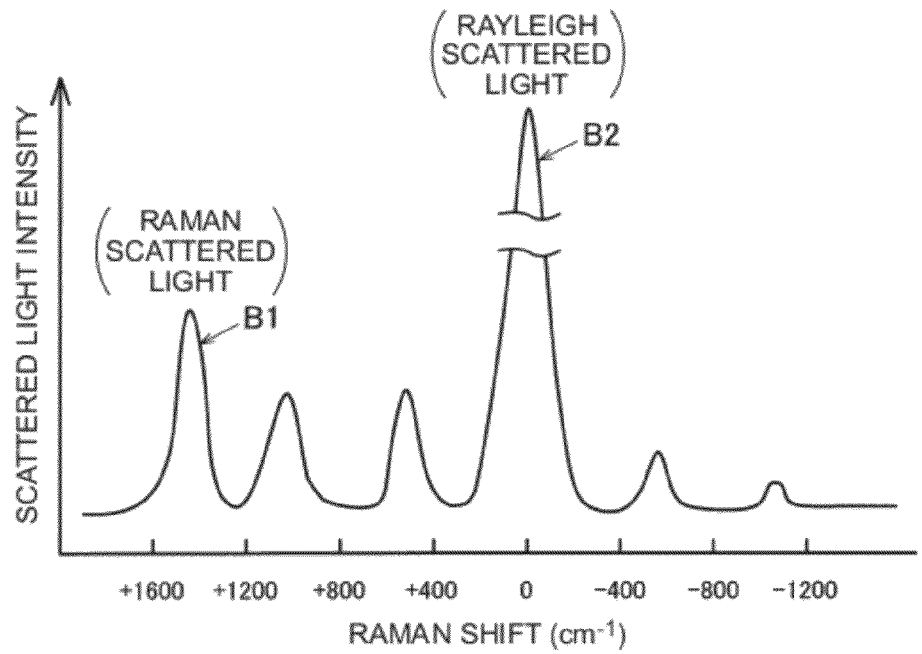
FIG. 4B is an example of Raman spectrum obtained by the Raman scattering spectroscopy.

FIG. 4B shows an example of Raman spectrum (a relationship between Raman shift and Raman scattering intensity) obtained by the Raman scattering spectroscopy. The lateral axis of the graph shown in FIG. 4B represents the Raman shift. The Raman shift denotes a difference between the wave number (the number of vibration) of the Raman scattered light Ram and the wave number of the incident light Lin, and takes a value unique to a molecular binding state of the target molecule X.

As shown in FIG. 4B, in comparison between a scattering intensity (spectrum peak) of the Raman scattered light Ram indicated by B1 and a scattering intensity of the Rayleigh scattered light Ray indicated by B2, it is understood that the Raman scattered light Ram is weaker. As described above, the Raman scattering spectroscopy is a measurement method, which is superior in identifiability of the target molecule X, but has a low sensitivity in sensing the target molecule X. Therefore, in the present embodiment, increase in sensitivity of a sensor is achieved using a spectroscopy by surface enhanced Raman scattering.

In order to realize a highly-sensitive surface plasmon resonance sensor making use of the surface enhanced Raman scattering, it is desirable that a degree of enhancement of a localized electrical field (hereinafter arbitrarily abbreviated as the degree of enhancement) is as high as possible. A degree of enhancement α is expressed as Formula (1) below (M. Inoue, K. Ohtaka, J. Phys. Soc. Jpn., 52, 3853 (1983)). Here, αray denotes the degree of enhancement in an excitation wavelength (equal to Rayleigh scattering wavelength), and αram denotes the degree of enhancement in Raman scattering wavelength.

$$\alpha = \alpha_{ray} \times \alpha_{ram} \quad (1)$$

Figure 5:
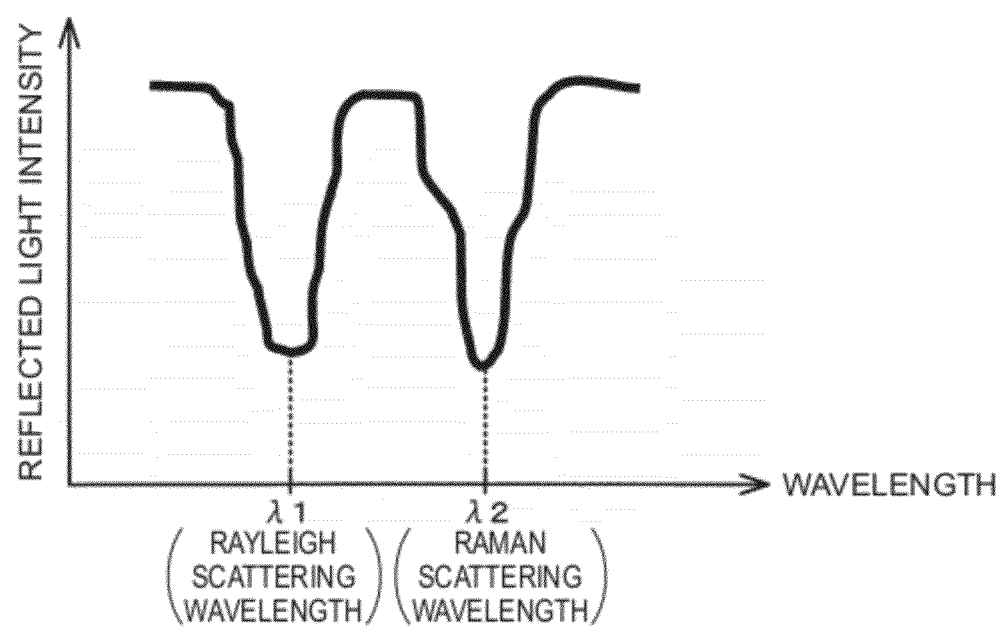
FIG. 5 is a characteristic diagram showing the Raman scattering spectroscopy for generating two intensive resonance peaks only in the vicinities of an excitation wavelength and Raman scattering wavelength.

According to Formula (1) described above, in order for raising the degree of enhancement in a surface enhanced Raman scattering process, it is necessary to simultaneously raise both of the degree of enhancement in an excitation process and the degree of enhancement in a Raman scattering process. For that purpose, in the present embodiment, two intensive resonance peaks are generated only in the vicinities of the excitation wavelength and the Raman scattering wavelength as shown in FIG. 5. Thus, it is possible to dramatically enhance an enhancement effect of the localized electrical field due to a synergistic effect of the both scattering processes.

Figure 9:
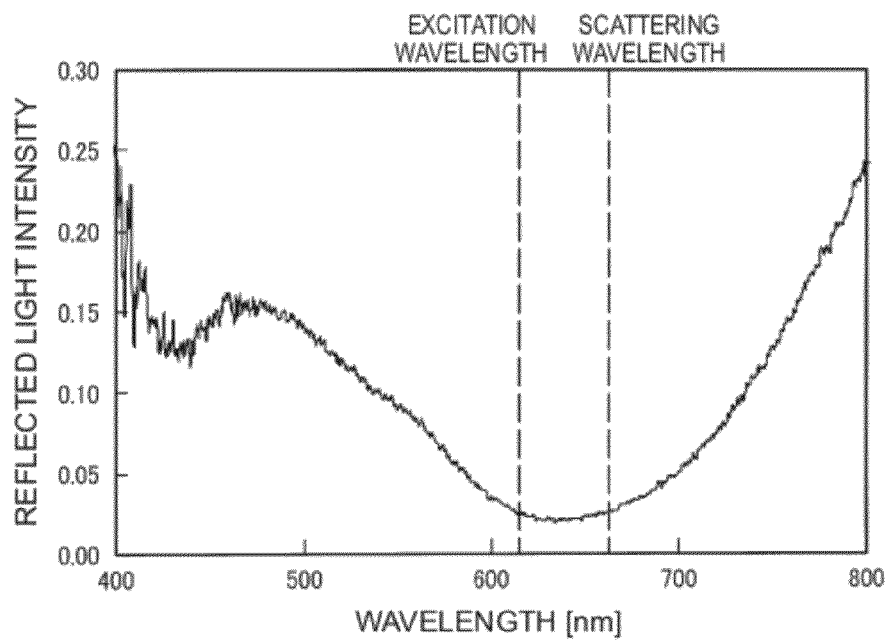
FIG. 9 is a characteristic diagram showing a spectral reflection intensity in the case in which a metal nanostructure does not have periodicity.

It should be noted that the present embodiment is preferably based on the principle described above, but is not limited to those generating the two resonance peaks (see FIG. 9 described later).

2. Optical Device

Figure 6A:
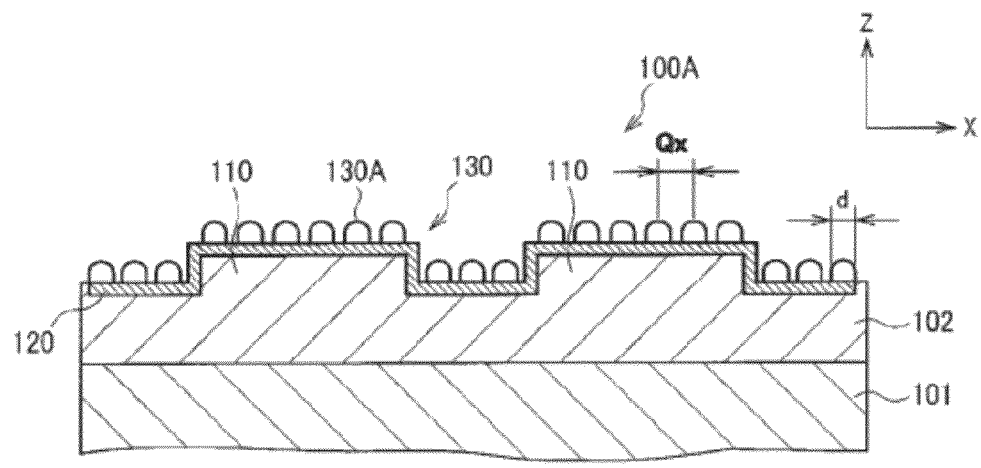
FIGS. 6A through 6C are diagrams schematically showing the structure of a surface plasmon resonance sensor chip according to the present embodiment for generating the two resonance peaks in the vicinities of the excitation wavelength and the Raman scattering wavelength.
Figure 6B:
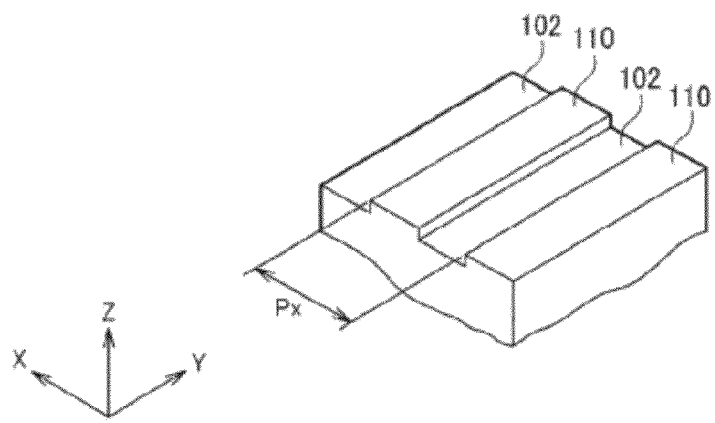
Figure 6C:
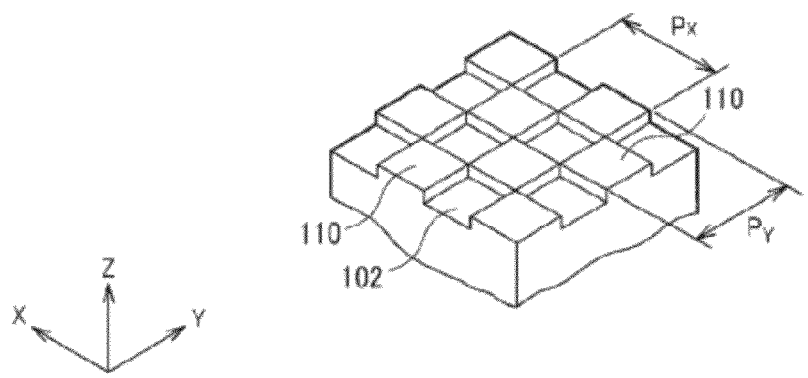

FIGS. 6A through 6C schematically show the structure of a surface plasmon resonance sensor chip (an optical device) 100A according to the present embodiment capable of generating the two resonance peaks respectively in the vicinities of the excitation wavelength and the Raman scattering wavelength. It should be noted that hereinafter the dimensions and the ratios of constituents are arbitrarily made different from actual elements in order for showing the constituents with visible sizes in the drawings.

FIG. 6A is a cross-sectional view of the whole of the chip structure, wherein the sensor chip 100A is for detecting the target object (the target material, the target molecule) using the surface plasmon resonance and the surface enhanced Raman scattering, and includes a substrate 101, a projection group 110, a dielectric layer 120, and a metal nanostructure 130 composed of a number of metal nanoparticles 130A.

It should be noted that although the case in which the sensor chip 100A is a metal grating made of metal will hereinafter be explained as an example, the present embodiment is not limited to this case. The sensor chip 100A is only required to be a grating made of an electrical conductor.

Specifically, the substrate 101 includes a metal surface (a conductor surface in a broad sense) 102 made of, for example, Ag (silver) or Au (gold), and is formed to have a plate like shape such as a rectangular shape or a circular shape. The substrate 101 can be what is obtained by, for example, forming a metal thin film on a glass substrate. The projection group 110 is arranged one-dimensionally at a pitch Px in at least a first direction X on the conductor surface 102 of the substrate 101, and is formed from, for example, the same metal (conductor) as that of the conductor surface 102. The sensor chip 100A can be formed as a metal grating having one-dimensional or two-dimensional periodicity as described later (see FIGS. 6B and 6C).

More specifically, each of projections of the projection group 110 is formed so that the cross-sectional shape thereof in the arrangement direction X of the projections is a convex shape projecting from the conductor surface 102 of the substrate 101. The convex shape includes a rectangle, a trapezoid, a circular arc, and so on. For example, as shown in FIG. 6B, the projection group 110 can have a one-dimensional grating structure formed as stripes parallel to each other in a second direction Y perpendicular to the first direction X in a plan view with respect to the substrate 101. In this case, by using a linearly polarized beam having a polarization direction perpendicular to a groove between the projections of the projection group 110 as an excitation light for an SP wave, the degree of enhancement of the electrical field can further be raised. Instead of the above, it is also possible for the projection group 110 to have a two-dimensional grating structure in which the projections are arranged in the first direction X at the period Px and in the second direction Y at a pitch Py in the plan view with respect to the substrate 101 as shown in FIG. 6C. In this case, by using a circular polarized beam as the excitation light for the SP wave, the degree of enhancement of the electrical field can further be enhanced. It is desirable that the pitch Px and the pitch Py are set in a range of 100 through 1000 nm, preferably in a range of 400 through 600 nm, and the height of the projections of the projection group 110 is set in a range of 10 through 100 nm.

The dielectric layer 120 made of, for example, $SiO_2$, which does not absorb the incident light, is formed by being applied in a stepped manner to a surface of the metal grating composed of the conductor surface 102 and the projection group 110. Further, the metal nanostructure 130 composed of a number of metal nanoparticles 130A each having a size d in a range of 1 through several hundreds of nanometers, preferably in a range of 10 through 100 nm, further preferably in a range of 20 through 60 nm is overlapped on the surface of the metal gratings 102, 110 having periodicity via the dielectric layer 120. In FIG. 6A, the metal nanostructure 130 can be arranged in the first direction X at a constant pitch Qx, or at a pitch no larger than a maximum pitch Qx in the case of having no periodicity. In other words, the metal nanostructure 130 is not necessarily required to have the periodicity, and the structure with the periodicity (Qx, Qy) in a vertical direction, a horizontal direction, or both of the vertical and horizontal directions and the structure without the periodicity can be adopted. Further, the metal nanostructure 130 having a shape with a distribution (variation) in size, and the metal nanostructure having a shape without the distribution can also be adopted. The constant pitch Qx (Qy) or the maximum pitch Qx (Qy) can be set to be equal to or smaller than 500 nm. Those fulfilling Px/10>Qx and Py/10>Qy can preferably be adopted. By adopting such a configuration, 10 or more metal nanoparticles 130A can be disposed within a single pitch Px (Py), and the density of the hot sites is raised.

Here, in the case of irradiating the metal nanoparticles 130A with a size d smaller than a wavelength λ of an incident light with the incident light, an electrical field of the incident light affects free electrons existing on surfaces of the metal nanoparticles 130A to cause resonance. Thus, electric dipoles due to the free electrons are excited in the metal nanoparticles 130A, and an enhanced electrical field stronger than the electrical field of the incident light is formed. This phenomenon is also called localized surface plasmon resonance (LSPR). This phenomenon is unique to an electrical conductor of the metal nanoparticles 130A having the sized (d=1 through several hundreds of nanometers) smaller than the wavelength of the incident light.

Figure 7:
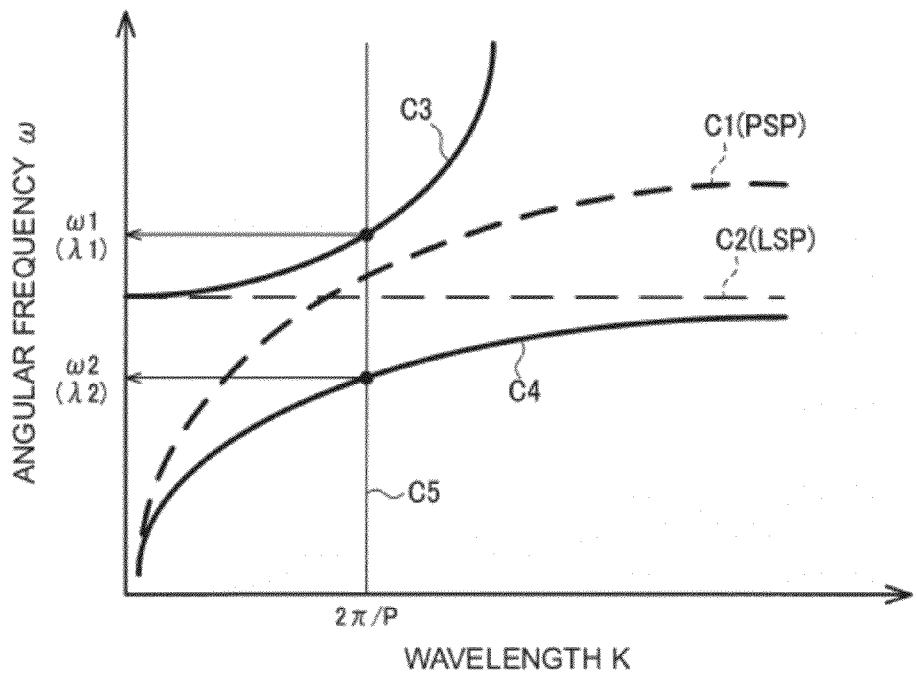
FIG. 7 is a characteristic diagram showing the setting of two resonance peak wavelengths in the sensor chip shown in FIG. 6A.

FIG. 7 is a dispersion curve of the sensor chip structure shown in FIG. 6A. FIG. 7 shows the wave number (the wave number of an evanescent wave) of a propagating surface plasmon PSP excited when irradiating the sensor chip structure with light having an angular frequency ω (the wavelength λ). Here, assuming that the pitches Px, Py shown in FIGS. 6B and 6C fulfill Px=Py=P, the wave number is 2π/P.

If a polarization direction of the incident light is made perpendicular to a groove direction of the grating, a vibration of an electromagnetic wave is excited with a vibration of the free electrons in the metal grating. Since the vibration of the electromagnetic wave affects the vibration of the free electrons, a surface plasmon polariton as a system obtained by combining the vibrations of the both parties is formed. The surface plasmon polariton is excited when the wave number 2π/P of the evanescent wave and the wave number of the propagating surface plasmon PSP become equal to each other.

FIG. 7 shows two dispersion curves C1, C2, one is a dispersion curve C1 of a localized surface plasmon SP excited in the metal nanostructure 130, the other is a dispersion curve C2 of the propagating surface plasmon PSP excited in an interface between the dielectric layer 120 and the metal grating 102, 110. In the present embodiment, since both of the metal grating 102, 110 and the metal nanostructure 130 are used, there can be obtained two points where the other two dispersion curves C3, C4 obtained by combining the two dispersion curves C1, C2, and a straight line passing through the wave number 2π/P intersect with each other.

Assuming that the pitch of the metal grating 102, 110 is P, it is understood that two surface plasmons SP excited in the wave number 2π/P exits. In other words, one of the surface plasmons SP resonates with light having an angular frequency ω1 (the wavelength λ1), and the other of the surface plasmons SP resonates with light having an angular frequency ω2 (the wavelength λ2).

By selecting a condition such as material and the size of the metal nanostructure 130, the material, the pitch P, the irregularity ratio, or the irregularity depth of the metal grating 102, 110, these resonance angular frequencies (the resonance wavelengths) can be tuned in to desired two angular frequencies (the wavelengths).

Figure 8:
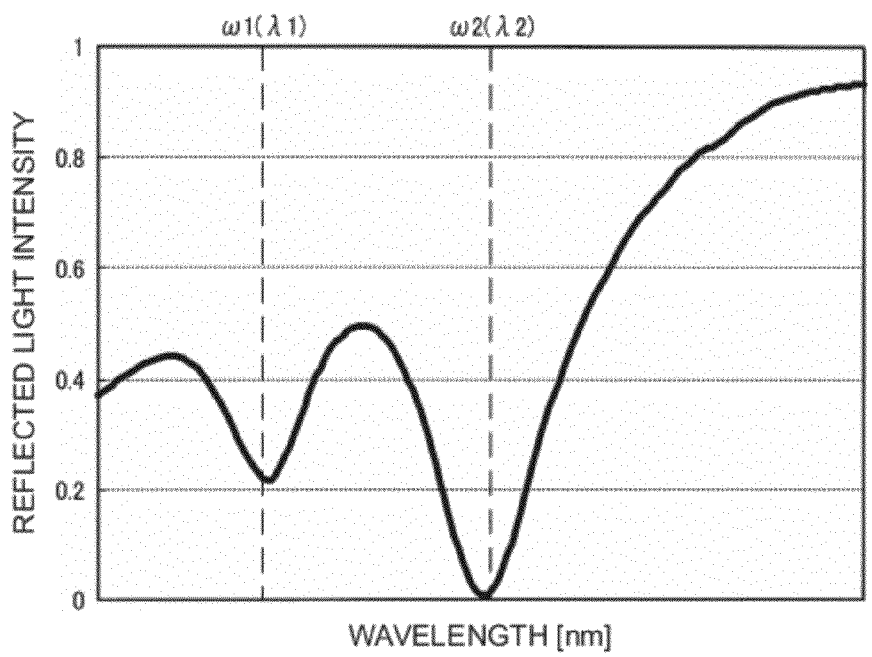
FIG. 8 is a characteristic diagram showing a reflected light intensity of the sensor chip shown in FIG. 6A.

FIG. 8 is a spectral reflection characteristic of the sensor chip structure shown in FIG. 6A. It is understood from FIG. 8 that there are two wavelengths at which a reflected light intensity dramatically drops. These two wavelengths λ1, λ2 correspond to the wavelengths λ1, λ2 shown in FIG. 5 above. In other words, in the resonant wavelengths λ1, λ2, energy of the incident light is used for exciting the SP wave, and therefore, the intensity of the reflected light is reduced. When using the sensor chip 100A shown in FIG. 6A, the resonant frequency λ1 is set to the excitation wavelength, and the resonant frequency λ2 is set to the scattering wavelength. In this case, a dramatic electrical field enhancement effect due to the surface plasmon resonance SPR can be obtained as described with reference to the Formula 1.

It should be noted that in the present embodiment, the metal nanostructure 130 is not necessarily required to have the periodicity. This is because, in the case in which the metal nanostructure 130 does not have the periodicity, the peak of the resonant wavelength in the spectral reflection characteristic becomes broad as shown in FIG. 9, however, since the peak includes the excitation wavelength and the scattering wavelength, the dramatic electrical field enhancement effect appears.

3. Optical Device Having Metal Nanostructure With No Periodicity

Figure 10:
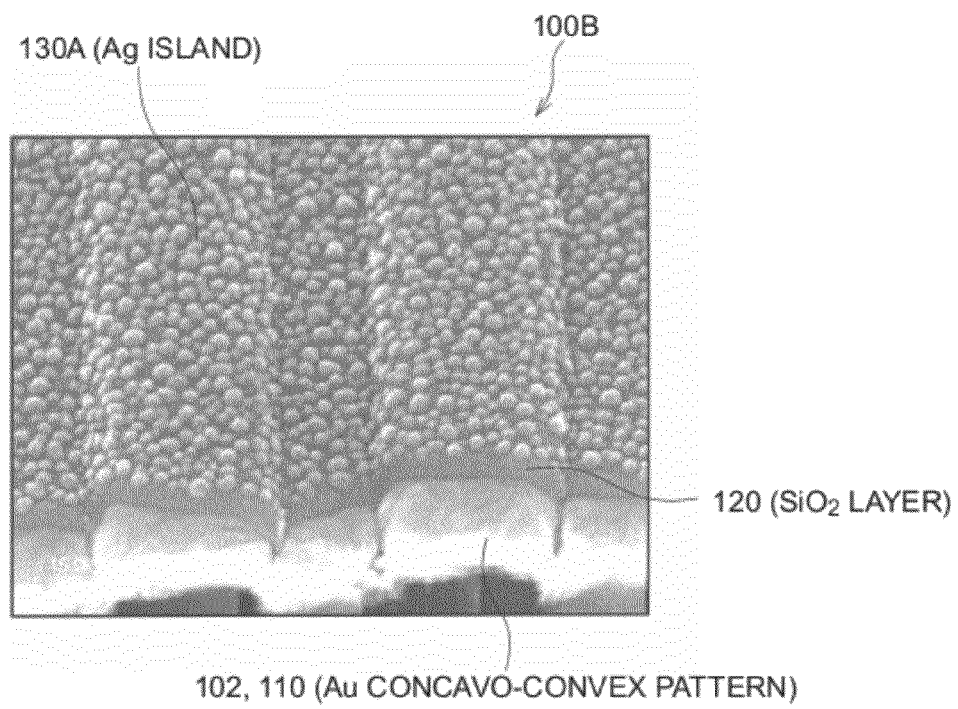
FIG. 10 is a diagram showing a sensor chip the metal nanostructure of which does not have periodicity.

FIG. 10 shows a specific example of a sensor chip (the optical device) 100B according to another embodiment of the invention. In this sensor chip 100B, metal nanoparticles 130A formed of Ag islands are formed on a surface of an Au concavo-convex pattern (a metal grating) 102, 110 via a $SiO_2$ layer (a dielectric layer) 120. There is a variation in size of Ag particles in the Ag island 130A in a range of 20 through 80 nm, and moreover, there is no periodicity. The thickness of the $SiO_2$ layer (the dielectric layer) is 40 nm. The Au concavo-convex pattern (the metal grating) 102, 110 has a periodicity only in one direction, and the pitch P thereof is 585 nm, the depth is 50 nm, and the irregularity ratio is roughly 7:3 (after depositing the $SiO_2$ layer).

Figure 11:
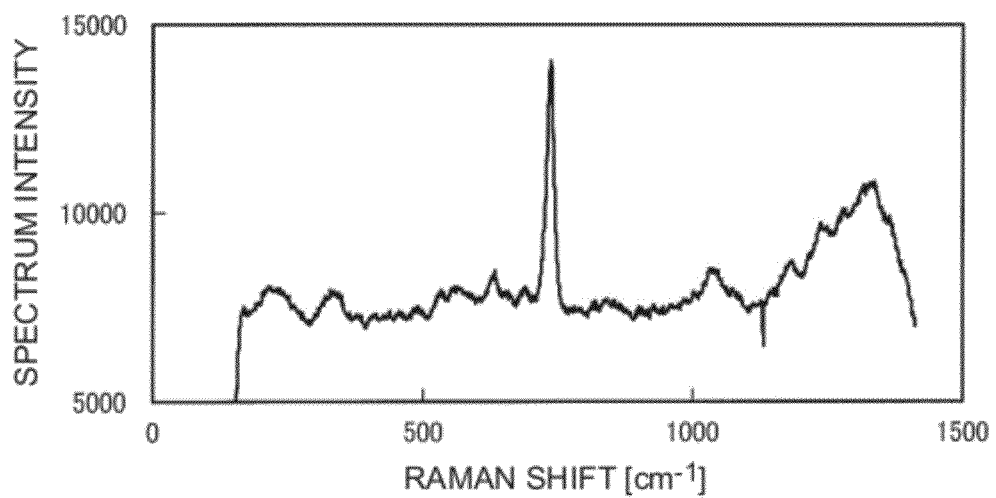
FIG. 11 is a diagram showing an example of Raman scattered light spectrum obtained using the sensor chip shown in FIG. 10.

FIG. 11 is a diagram showing an example of the Raman scattered light spectrum obtained using the sensor chip 100B shown in FIG. 10. An excitation light source is an He—Ne laser (with the wavelength of 633 nm), and a detection target sample on the sensor chip 100B is irradiated with a linearly polarized light beam emitted therefrom. The sample is an adenine molecule, and a signal peak (e.g., the wave number 730 $cm^{-1}$) unique to this molecule has been detected. The degree of enhancement of the electrical field in this detection is assumed to be roughly $10^7$. It should be noted that the polarization direction of the beam is set to be perpendicular to grooves of the Au concave-convex pattern (the metal grating) 102, 110.

Figure 12:
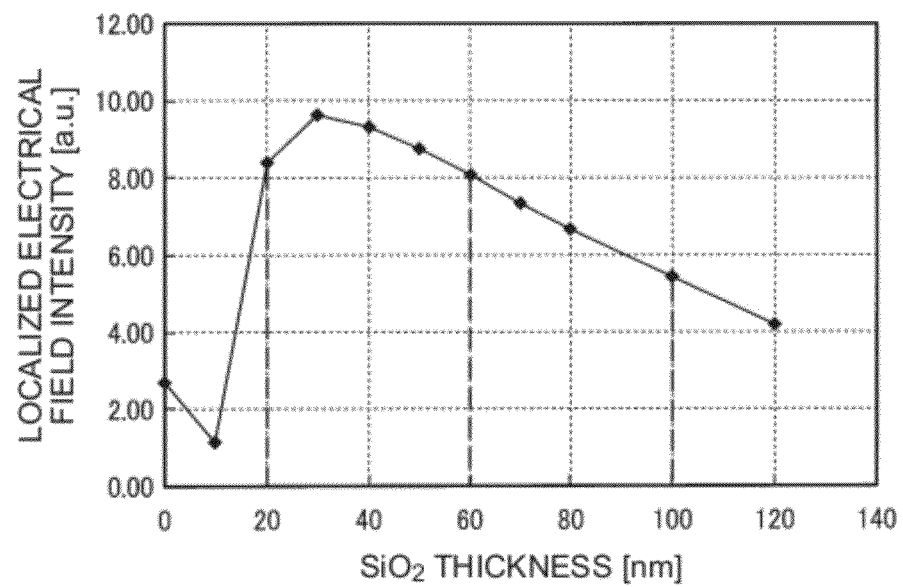
FIG. 12 is a characteristic diagram showing a relationship between an electromagnetic field intensity and a dielectric layer.

The degree of enhancement of the electrical field of the sensor chip 100B significantly depends on the thickness of the $SiO_2$ layer 120. FIG. 12 shows a relationship between an intensity of the signal peak of the wave number 730 $cm^{-1}$ and the thickness of the $SiO_2$ layer 120. According to the drawing, it is understood that the degree of enhancement of the electrical field becomes maximum with the thickness of the $SiO_2$ layer 120 of around 40 nm. By setting the thickness of the dielectric film 120 to be equal to or smaller than 100 nm, or preferably in a range of 20 through 60 nm, an intensity of a localized magnetic field can be kept to be higher than a certain level. It should be noted that a result shown in FIG. 12 is obtained from a flat Au film. This is because, if the Au concave-convex pattern 102, 110 is used, since the irregularity ratio of the pattern is changed in accordance with the change in the thickness of the $SiO_2$ layer 120, it is difficult to find out the effect of the $SiO_2$ layer 120 alone.

4. Method of Manufacturing Optical Device

Figure 13A:
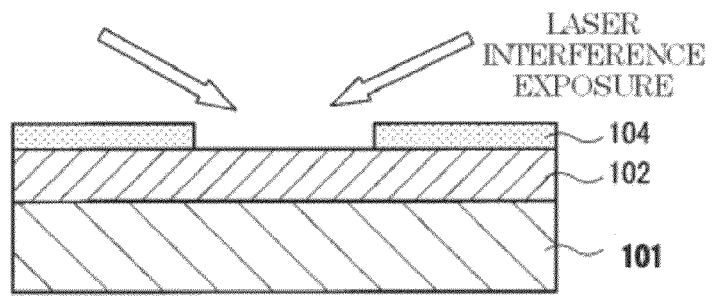
FIGS. 13A through 13D are diagrams showing a method of manufacturing the sensor chip shown in FIG. 6A.
Figure 13B:
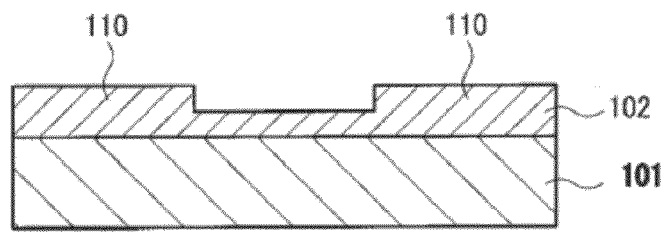
Figure 13C:
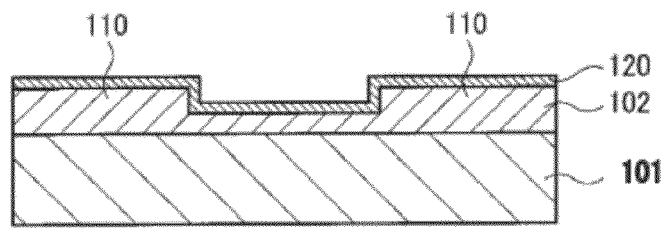
Figure 13D:
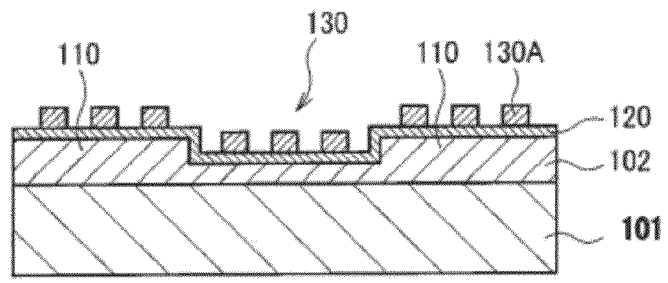

FIGS. 13A through 13D show a method of manufacturing the sensor chip 100A shown in FIG. 6A. Firstly, as shown in FIG. 13A, the Au layer 102 is formed on a $SiO_2$ substrate 101, and then a resist pattern 104 is formed on the Au layer 102 using a laser interference exposure. Subsequently, as shown in FIG. 13B, the Au layer 102 on the SiO$_2$ substrate 101 is dry-etched using the resist pattern 104 as a mask. Subsequently, as shown in FIG. 13C, the SiO$_2$ layer 120 is deposited on the Au layer 102 by sputtering. Finally, as shown in FIG. 13D, the Ag islands 130 are formed on the SiO$_2$ layer 120 using the heated vacuum evaporation to thereby form the metal nanostructure 130. In this case, as shown in FIG. 10, the Ag islands 130A have non-uniform shapes, a distribution in size, and does not have the shapes with a periodicity.

Figure 14A:
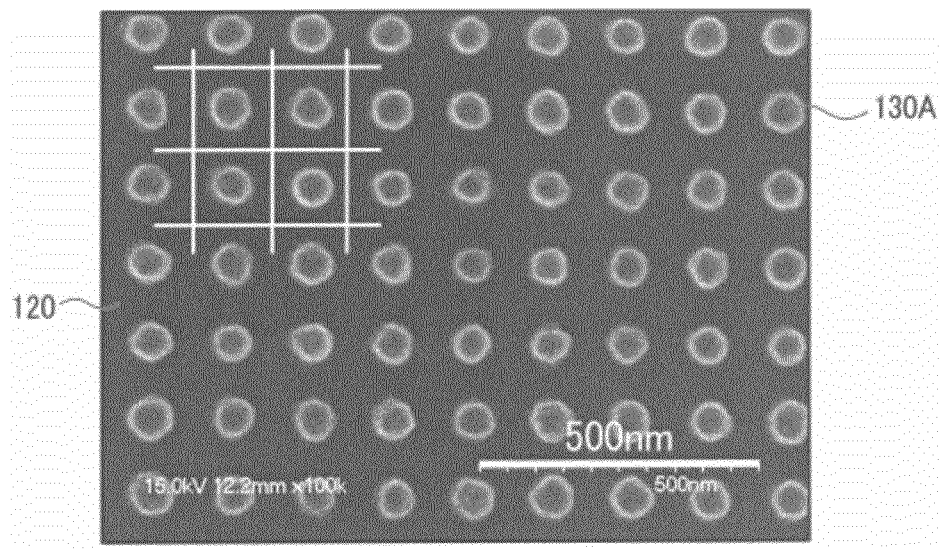
FIGS. 14A and 14B are diagrams showing a periodic arrangement of the metal nanoparticles.
Figure 14B:
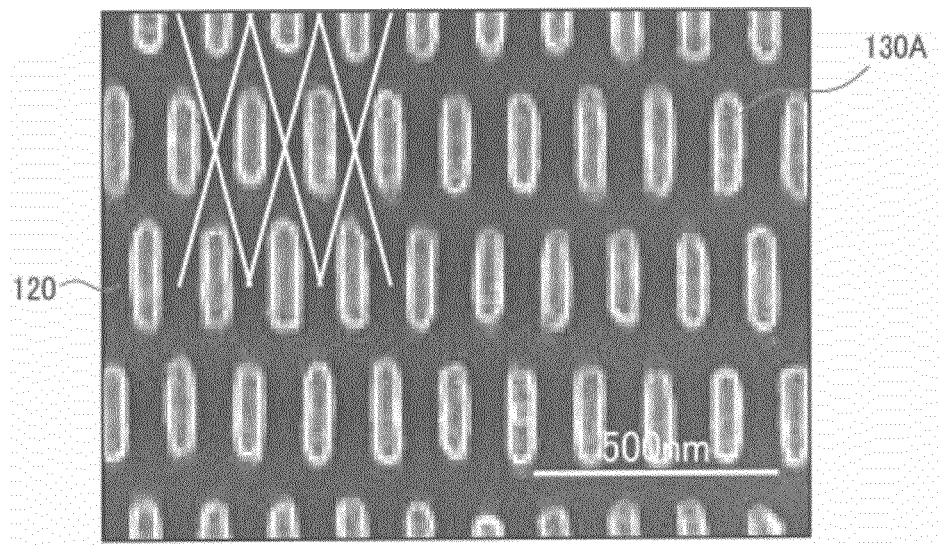

Further, it is also possible to arrange the metal nanoparticles 130A with the one-dimensional pitch Qx as shown in FIG. 6A, or to form the metal nanoparticles 130A each having a dot shape or a long ellipsoidal shape on the dielectric layer 120 at two-dimensional pitches Qx, Qy (not shown) as shown in FIGS. 14A, 14B. In this case, it is possible to form the metal nanostructure 130 by repeating the laser interference exposure and the dry etching. Further, although the material of the metal nanostructure 130 and the material of the conductor surface 102 are metals different from each other, it is also possible to use the combination of the same metal.

5. Detection Device

Figure 15:
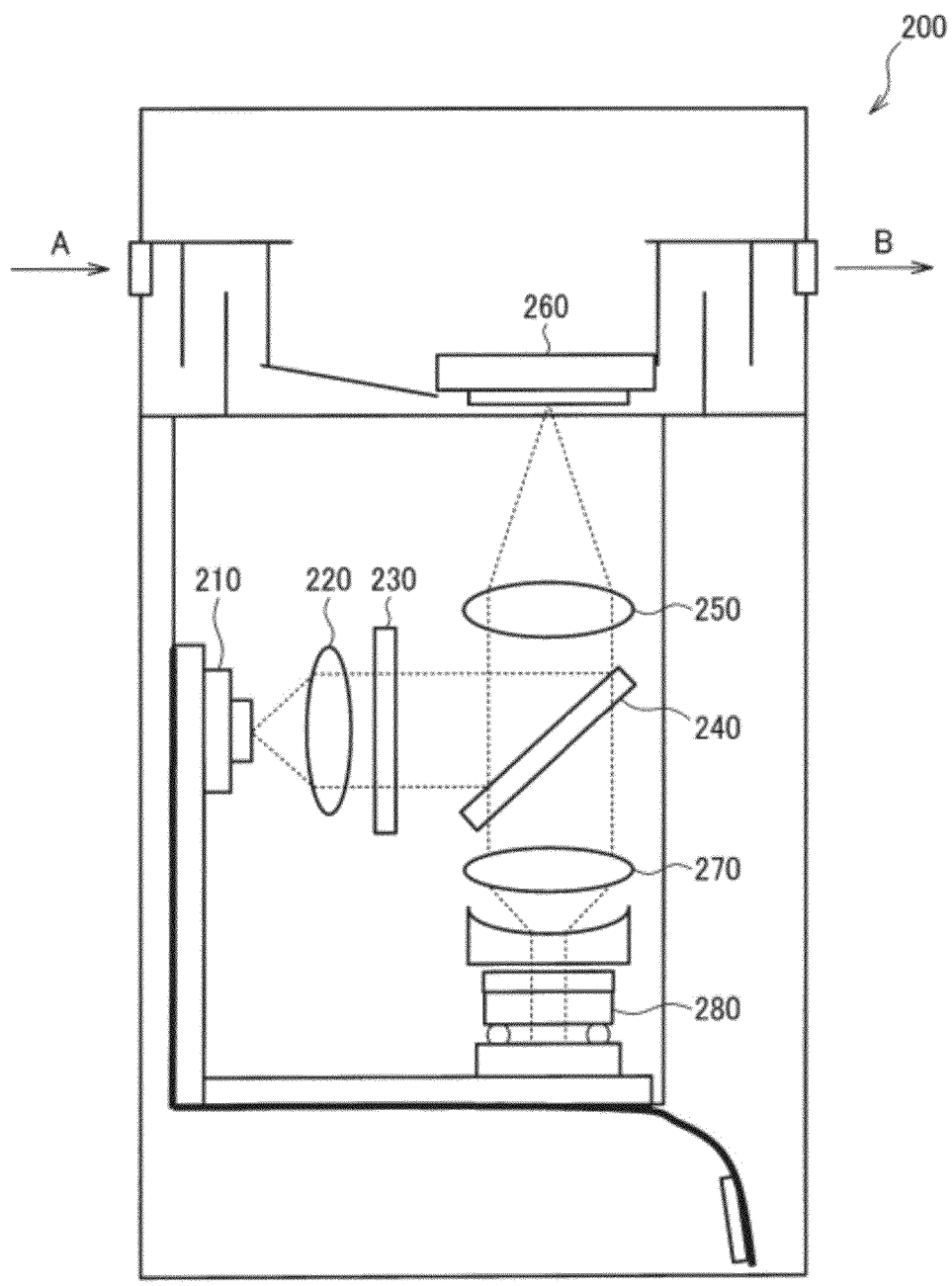
FIG. 15 is a diagram showing a detection device.

FIG. 15 is a schematic diagram showing an example of a detection device 200 provided with one of the sensor chips (the optical devices) 100A and 100B described above. A target material (not shown) is carried in the detection device 200 from a direction A, and then carried out to a direction B. A laser emitted from an excitation light source 210 is collimated by a collimator lens, transmitted through a polarization control element 230, and then guided in a direction toward a sensor chip 260 by a dichroic mirror 240. The laser is collected by an objective lens 250, and then enters the sensor chip 260. On this occasion, the target material (not shown) is disposed on a surface (e.g., a surface on which the metal nanostructure 130 is formed) of the sensor chip 260. It should be noted that it is arranged that by controlling the drive of a fan (not shown), the target material is introduced from a carry-in port into the inside of a carrying section, and then discharged outside the carrying section from a discharge port.

When the laser beam enters the surface of the sensor chip 260, an extremely strong enhanced electrical field is generated in the vicinity of the metal nanostructure 130 via a surface plasmon resonance SPR. When one through several pieces of target material enter the enhanced electrical field, the Raman scattered light is generated there. The Raman scattered light is transmitted through the objective lens 250, then guided to a direction toward a light detector 280 by the dichroic mirror 240, then collected by a collecting lens 270, and then enters the light detector 280. Subsequently, a spectral decomposition is performed by the light detector 280, and then spectrum information as shown in FIG. 11 can be obtained. According to this configuration, since the sensor chip 100A or 100B described above is provided, the sensor sensitivity is enhanced, and it becomes possible to identify the target material based on the Raman spectrum.

It should be noted that although the present embodiment is hereinabove explained in detail, it should easily be understood by those skilled in the art that various modifications not substantially departing from the novel matters and the effects of the invention are possible. Therefore, such modified examples should be included in the scope of the invention.

The entire disclosure of Japanese Patent Application No. 2011-139526, filed Jun. 23, 2011 is expressly incorporated by reference herein.

What is claimed is:

1. An optical device comprising:
a group of projections projecting from a conductor surface of a substrate, and arranged along a first direction at a pitch Px;
a dielectric layer covering the conductor surface and the group of projections; and
a metal nanostructure having metal nanoparticles each having a size d of the order of nanometers arranged on the dielectric layer along the first direction,
wherein assuming that the wavelength of irradiation light is $\lambda$, $\lambda > Px > d$ is fulfilled, and
assuming that a maximum value of an arrangement pitch between two of the metal nanoparticles adjacent to each other in the first direction is Qx, Px>Qx is fulfilled.

2. The optical device according to claim 1, wherein Px/10>Qx is fulfilled, and ten or more of the metal nanoparticles are arranged within the pitch Px along the first direction.

3. The optical device according to claim 1, wherein the group of projections are arranged along a second direction perpendicular to the first direction at a pitch Py, $\lambda > Py > d$ is fulfilled, and
assuming that a maximum value of an arrangement pitch between two of the metal nanoparticles adjacent to each other in the second direction is Qy, Py>Qy is fulfilled.

4. The optical device according to claim 3, wherein Py/10>Qy is fulfilled, and ten or more of the metal nanoparticles are arranged within the pitch Py along the second direction.

5. The optical device according to claim 1, wherein the metal nanoparticles are arranged in the first direction at a constant pitch Qx.

6. The optical device according to claim 3, wherein the metal nanoparticles are arranged in the second direction at a constant pitch Qy.

7. The optical device according to claim 1, wherein a thickness of the dielectric layer is equal to or smaller than 100 nm.

8. A detection device comprising:
the optical device according to claim 1;
a light source; and
a light detection section,
wherein a sample is introduced in the metal nanostructure of the optical device,
the optical device emits light reflecting the sample in response to irradiation of light from the light source, and
the light detection section detects the light reflecting the sample from the optical device.

9. A detection device comprising:
the optical device according to claim 2;
a light source; and
a light detection section,
wherein a sample is introduced in the metal nanostructure of the optical device,
the optical device emits light reflecting the sample in response to irradiation of light from the light source, and
the light detection section detects the light reflecting the sample from the optical device.

10. A detection device comprising:
the optical device according to claim 3;
a light source; and
a light detection section,
wherein a sample is introduced in the metal nanostructure of the optical device,
the optical device emits light reflecting the sample in response to irradiation of light from the light source, and the light detection section detects the light reflecting the sample from the optical device.

11. A detection device comprising:
the optical device according to claim 4;
a light source; and
a light detection section,
wherein a sample is introduced in the metal nanostructure of the optical device,
the optical device emits light reflecting the sample in response to irradiation of light from the light source, and
the light detection section detects the light reflecting the sample from the optical device.

12. A detection device comprising:
the optical device according to claim 5;
a light source; and
a light detection section,
wherein a sample is introduced in the metal nanostructure of the optical device,
the optical device emits light reflecting the sample in response to irradiation of light from the light source, and
the light detection section detects the light reflecting the sample from the optical device.

13. A detection device comprising:
the optical device according to claim 6;
a light source; and
a light detection section,
wherein a sample is introduced in the metal nanostructure of the optical device,
the optical device emits light reflecting the sample in response to irradiation of light from the light source, and
the light detection section detects the light reflecting the sample from the optical device.

14. A detection device comprising:
the optical device according to claim 7;
a light source; and
a light detection section,
wherein a sample is introduced in the metal nanostructure of the optical device,
the optical device emits light reflecting the sample in response to irradiation of light from the light source, and
the light detection section detects the light reflecting the sample from the optical device.

* * * * *